US012053496B2

United States Patent
Kawaguchi et al.

(10) Patent No.: US 12,053,496 B2
(45) Date of Patent: Aug. 6, 2024

(54) **AGENT FOR PREVENTION AND/OR TREATMENT OF *PSEUDOMONAS AERUGINOSA* INFECTION**

(71) Applicant: Nutri Co., Ltd., Yokkaichi (JP)

(72) Inventors: Susumu Kawaguchi, Yokkaichi (JP); Miho Kato, Yokkaichi (JP)

(73) Assignee: Nutri Co., Ltd., Yokkaichi (JP)

( * ) Notice: Subject to any disclaimer, the term of this patent is extended or adjusted under 35 U.S.C. 154(b) by 1 day.

(21) Appl. No.: 16/980,938

(22) PCT Filed: Apr. 17, 2019

(86) PCT No.: PCT/JP2019/016441
§ 371 (c)(1),
(2) Date: Sep. 15, 2020

(87) PCT Pub. No.: WO2019/203260
PCT Pub. Date: Oct. 24, 2019

(65) Prior Publication Data
US 2020/0405784 A1    Dec. 31, 2020

(30) Foreign Application Priority Data

Apr. 19, 2018   (JP) ................................. 2018-080756

(51) Int. Cl.
| | | |
|---|---|---|
| *A61K 39/02* | (2006.01) | |
| *A23L 33/135* | (2016.01) | |
| *A61K 35/744* | (2015.01) | |
| *A61K 39/108* | (2006.01) | |
| *A61P 31/04* | (2006.01) | |

(52) U.S. Cl.
CPC .......... *A61K 35/744* (2013.01); *A23L 33/135* (2016.08); *A61P 31/04* (2018.01)

(58) Field of Classification Search
None
See application file for complete search history.

(56) References Cited

U.S. PATENT DOCUMENTS

| | | |
|---|---|---|
| 2014/0186409 A1 | 7/2014 | Lang et al. |
| 2019/0053527 A1* | 2/2019 | Jeantet .................... C12N 1/04 |

FOREIGN PATENT DOCUMENTS

| | | | |
|---|---|---|---|
| CN | 1386510 A | 12/2002 | |
| CN | 103502434 A | 1/2014 | |
| JP | H08-283166 A | 10/1996 | |
| JP | 2002-179580 A | 6/2002 | |
| JP | 2003-261453 A | 9/2003 | |
| JP | 2014-513106 A | 5/2014 | |
| WO | 2009098520 A | * 8/2009 | |

OTHER PUBLICATIONS

English translation of Nichinchi, Seiyaku (JP H08 283166; Oct. 29, 1996 ) cited by Applicants on IDS Jan. 11, 2022.*
English translation of Gu, Z (JP 2002-179580 A Jun. 26, 2002; cited by Applicants on IDS Sep. 15, 2020.*
Nichinchi, Seiyaku (JP HO8 283166); machine translation from the WIPO IP Portal. Oct. 29, 1996. pages 1-5.*
https://patentscope.wipo.int/search/en/detail.jsf?docId=JP267041592 &_cid=P22-LAMZB5-72484-1 Oct. 29, 1996.*
Extended European Search Report issued in corresponding European Patent Application No. 19788978.5 dated Dec. 3, 2021.
International Search Report issued in corresponding International Patent Application No. PCT/JP2019/016441 dated May 21, 2019.
Garcia-Cano et al., "Antibacterial activity produced by Enterococcus spp. isolated from an artisanal Mexican dairy product, Cotija cheese," Food Science and Technology, 59: 26-34 (2014).
Mendoza et al., "Characterization of a bacteriocin produced by enterococcus gallinarum CRL 1826 isolated from captive bullfrog: Evaluation of its mode of action against Listeria monocytogenes and gram-negatives," Journal of Bioprocessing & Biotechniques, 5 (8): 1-9 (2015).

* cited by examiner

*Primary Examiner* — Jennifer E Graser
(74) *Attorney, Agent, or Firm* — Morgan, Lewis & Bockius LLP

(57) ABSTRACT

Provided is a novel prophylactic and/or therapeutic agent for *Pseudomonas aeruginosa* infection. It was found that a bacterium belonging to the genus *Enterococcus* can prevent and/or treat *Pseudomonas aeruginosa* infection. The prophylactic and/or therapeutic agent for *Pseudomonas aeruginosa* infection, comprising a bacterium belonging to the genus *Enterococcus*. A medicine for prevention and/or treatment of *Pseudomonas aeruginosa* infection, comprising a bacterium belonging to the genus *Enterococcus*. A food for prevention and/or treatment of *Pseudomonas aeruginosa* infection, comprising a bacterium belonging to the genus *Enterococcus*.

20 Claims, 6 Drawing Sheets

AGENT FOR PREVENTION AND/OR TREATMENT OF *PSEUDOMONAS AERUGINOSA* INFECTION

TECHNICAL FIELD

The present invention relates to a prophylactic and/or therapeutic agent for *Pseudomonas aeruginosa* infection.

BACKGROUND ART

*Pseudomonas aeruginosa* is a Gram-negative, rod-shaped bacterium that is ubiquitous in living environments such as kitchen, bathroom and other wet areas and it is one of less virulent bacteria that are usually non-pathogenic to healthy persons.

*P aeruginosa* shows natural resistance to the first generation cephem drugs (such as penicillin and cefazolin) and it also has a strong tendency to show resistance to antibacterial drugs such as tetracycline or macrolide antibiotics. This organism has posed the problem of causing opportunistic infections such as postoperative infection in patients with reduced ability of phylaxis. Further, multidrug resistant *P. aeruginosa* infections have also been confirmed, leading to the emergence of multidrug resistant bacteria due to inappropriate use of antimicrobial drugs (antibiotics). Occurrence of hospital-acquired (opportunistic) infections by *P aeruginosa* has become a social problem especially in hospitals and elderly care facilities with large numbers of immunocompromised patients.

DISCLOSURE OF THE INVENTION

Problem for Solution by the Invention

It is an object of the present invention to provide a novel, prophylactic and/or therapeutic agent for *Pseudomonas aeruginosa* infection.

Means to Solve the Problem

As a result of intensive efforts, the present inventors have found that a lactic acid bacterium belonging to the genus *Enterococcus* can prevent and/or treat *Pseudomonas aeruginosa* infection; the present invention has been achieved based on this finding.

The gist of the present invention is as follows.

(1) A prophylactic and/or therapeutic agent for *Pseudomonas aeruginosa* infection, comprising a bacterium belonging to the genus *Enterococcus*.

(2) The prophylactic and/or therapeutic agent for *Pseudomonas aeruginosa* infection of (1), wherein the bacterium belonging to the genus *Enterococcus* is a *Lactococcus*.

(3) The prophylactic and/or therapeutic agent for *Pseudomonas aeruginosa* infection of (2), wherein the *Lactococcus* is *Enterococcus fecalis*.

(4) The prophylactic and/or therapeutic agent for *Pseudomonas aeruginosa* infection of (3), wherein the *Enterococcus fecalis* is EF-2001 strain.

(5) The prophylactic and/or therapeutic agent for *Pseudomonas aeruginosa* infection of any one of (1)-(4), wherein the bacterium belonging to the genus *Enterococcus* is killed.

(6) The prophylactic and/or therapeutic agent for *Pseudomonas aeruginosa* infection of any one of (1)-(5), wherein the bacterium belonging to the genus *Enterococcus* is orally administered.

(7) The prophylactic and/or therapeutic agent for *Pseudomonas aeruginosa* infection of (6), wherein the bacterium belonging to the genus *Enterococcus* is orally administered in an amount of $1 \times 10^8$-$1 \times 10^{11}$ CFU/kg body weight per dose.

(8) The prophylactic and/or therapeutic agent for *Pseudomonas aeruginosa* infection of (7), wherein the bacterium belonging to the genus *Enterococcus* is orally administered one or more times per day in an amount of $1 \times 10^8$-$1 \times 10^{11}$ CFU/kg body weight per dose.

(9) The prophylactic and/or therapeutic agent for *Pseudomonas aeruginosa* infection of (8), wherein the bacterium belonging to the genus *Enterococcus* is orally administered one to five times per day in an amount of $1 \times 10^8$-$1 \times 10^{11}$ CFU/kg body weight per dose.

(10) The prophylactic and/or therapeutic agent for *Pseudomonas aeruginosa* infection of (6), wherein the bacterium belonging to the genus *Enterococcus* is orally administered in an amount of $1 \times 10^9$-$5 \times 10^{10}$ CFU/kg body weight per dose.

(11) The prophylactic and/or therapeutic agent for S *Pseudomonas aeruginosa* infection of (10), wherein the bacterium belonging to the genus *Enterococcus* is orally administered one or more times per day in an amount of $1 \times 10^9$-$5 \times 10^{10}$ CFU/kg body weight per dose.

(12) The prophylactic and/or therapeutic agent for *Pseudomonas aeruginosa* infection of (11), wherein the bacterium belonging to the genus *Enterococcus* is orally administered one to five times per day in an amount of $1 \times 10^9$-$5 \times 10^{10}$ CFU/kg body weight per dose.

(13) The prophylactic and/or therapeutic agent for *Pseudomonas aeruginosa* infection of (6), wherein the bacterium belonging to the genus *Enterococcus* is orally administered in an amount of $1.2 \times 10^{10}$ or more CFU/kg body weight per dose.

(14) The prophylactic and/or therapeutic agent for *Pseudomonas aeruginosa* infection of (13), wherein the bacterium belonging to the genus *Enterococcus* is orally administered one or more times per day in an amount of $1.2 \times 10^{10}$ or more CFU/kg body weight per dose.

(15) The prophylactic and/or therapeutic agent for *Pseudomonas aeruginosa* infection of (14), wherein the bacterium belonging to the genus *Enterococcus* is orally administered one to five times per day in an amount of $1.2 \times 10^{10}$ or more CFU/kg body weight per dose.

(16) The prophylactic and/or therapeutic agent for *Pseudomonas aeruginosa* infection of any one of (6)-(15), wherein the bacterium belonging to the genus *Enterococcus* is orally administered for seven or more days.

(17) The prophylactic and/or therapeutic agent for *Pseudomonas aeruginosa* infection of any one of (1)-(16), which is used for prevention of *Pseudomonas aeruginosa* infection.

(18) The prophylactic and/or therapeutic agent for *Pseudomonas aeruginosa* infection of any one of (1)-(16), which is used for treatment of *Pseudomonas aeruginosa* infection.

(19) A medicine for prevention and/or treatment of *Pseudomonas aeruginosa* infection, comprising a bacterium belonging to the genus *Enterococcus*.

(20) A food for prevention and/or treatment of *Pseudomonas aeruginosa* infection, comprising a bacterium belonging to the genus *Enterococcus*.

(21) A method for prevention and/or treatment of *Pseudomonas aeruginosa* infection, comprising administering to a subject a pharmaceutically effective amount of a bacterium belonging to the genus *Enterococcus*.

(22) Use of a bacterium belonging to the genus *Enterococcus* for prevention and/or treatment of *Pseudomonas aeruginosa* infection.

(23) A bacterium belonging to the genus *Enterococcus* for use in a method for prevention and/or treatment of *Pseudomonas aeruginosa* infection.

Effect of the Invention

The present invention enables prevention and/or treatment of *Pseudomonas aeruginosa* infection.

The present specification encompasses the contents of the specification and/or drawings disclosed in Japanese Patent Application No. 2018-80756 based on which the present application claims priority.

BEST MODES FOR CARRYING OUT THE INVENTION

Figure 1:
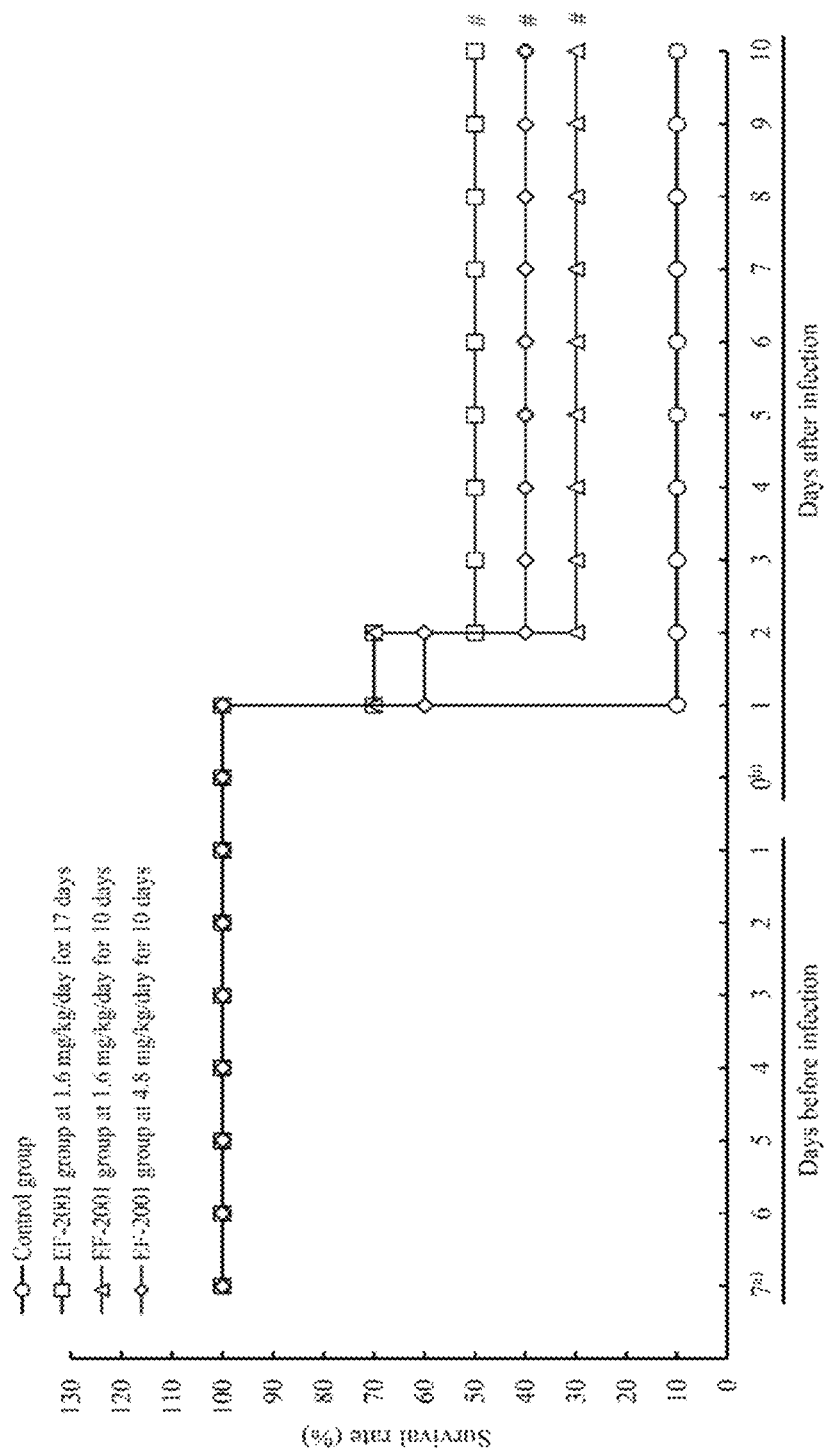
FIG. 1 shows test results (survival rate (results of Kaplan-Meier plot)) in Example 1.

Hereinafter, embodiments of the present invention will be described in more detail.

The present invention provides a prophylactic and/or therapeutic agent for *Pseudomonas aeruginosa* infection, comprising a bacterium belonging to the genus *Enterococcus*.

It is recommended that the bacterium belonging to the genus *Enterococcus* be a *Lactococcus* (e.g., *Enterococcus faecalis, Enterococcus faecium, Enterococcus avium, Enterococcus gallinarum*, or *Enterococcus casseliflavus*), and preferred is a *Lactococcus* having biological response modifier (BRM) activity (YAKUGAKU ZASSHI, 112: 919-925, 1992; YAKUGAKU ZASSHI, 113: 396-399, 1992; Journal of Animal Clinical Research, 3: 11-20, 1994). *Enterococcus faecalis* is known as a *Lactococcus* having BRM activity. *Enterococcus faecalis* EF-2001 strain is available from Nihon Berumu Co., Ltd. (2-14-3 Nagatacho, Chiyoda-ku, Tokyo).

*Enterococcus Faecalis*-2001 strain can be obtained from fecal matter of a normal person and has the following properties.

A Gram-positive coccus. Shape of colony (Trypto-Soya agar medium, 24-hour culture): 1.0-mm diameter, smooth, precise circle, white colony. Bacterial morphology: circular to oval (1.0×1.5 µm). Likely to form chains in liquid media. Non-spore-forming. Facultative anaerobic. Ferments glucose to produce lactic acid (final pH: 4.3). Non-gas-producing. Catalase-negative. Proliferates at 10 to 45° C. (the optimal temperature is 37° C.). Proliferates to pH 9.6, 6.5% NaCl, and 40% bile. Positive for 0.04% potassium tellurite. Positive for 0.01% tetrazolium. Positive for 0.1% methylene blue milk. Hydrolyzes arginine. Ferments amygdalin, cellobiose, fructose, galactose, glucose, glycerol, lactose, maltose, mannose, mannitol, ribose, salicin, sucrose, melicitose, and sorbitol to produce acids. Resistant at 60° C. for 30 minutes. Digests casein and gelatin. Decarboxylates tyrosine into tyramine. Lancefield antigen group: D. GC %: 35.0±1.0%.

The bacterium belonging to the genus *Enterococcus* may be a viable bacterium or a killed bacterium, and the bacterium may be subjected to a destruction treatment (e.g., homogenization, enzyme treatment, or ultrasonication) or any other treatment such as heating or drying (e.g., freeze-drying or spray-drying). The viable bacterium may be killed by heating. The viable bacterium is expected to exhibit effects produced by lactic acid fermentation. The killed bacterium is expected to exhibit an intestinal immunity-activating effect. The particle size of the bacterial cell is typically 0.05 µm-50 µm, preferably 0.08-20 µm, more preferably 0.1-10 µm. The bacterium may be mixed with a diluent, and then a thickener may be added to form granules. It is recommended to select the diluent and thickener from materials approved for addition to foods and medicines.

The prophylactic and/or therapeutic agent for *Pseudomonas aeruginosa* infection of the present invention can be used for phylaxis of *Pseudomonas aeruginosa* infection. As used herein, the term "phylaxis" refers to a concept encompassing not only prevention but also treatment of infection. The prophylactic and/or therapeutic agent for *Pseudomonas aeruginosa* infection of the present invention can be used as a medicine or a food additive. *Pseudomonas aeruginosa* may be multidrug resistant *P aeruginosa*.

The present invention provides a medicine for prevention and/or treatment of *Pseudomonas aeruginosa* infection, comprising a bacterium belonging to the genus *Enterococcus*.

When the agent is used as a medicine, it is recommended that the bacterium belonging to the genus *Enterococcus* be used alone or be mixed with an excipient or a carrier to make a formulation such as a tablet, a capsule, a powder, a granule, a liquid, a syrup, an aerosol, a suppository, or an injection. The excipient or carrier may be any excipient or carrier that is commonly used in the art and is pharmaceutically acceptable, and the type and composition of the excipient or carrier are chosen as appropriate. For example, water or a vegetable oil is used as a liquid carrier. As a solid carrier there is used, for example, a sugar such as lactose, sucrose, or glucose, a starch such as potato starch or corn starch, or a cellulose derivative such as crystalline cellulose. A lubricant such as magnesium stearate, a binder such as gelatin or hydroxypropyl cellulose, and a disintegrant such as carboxymethyl cellulose may also be added. Further, an antioxidant, a colorant, a flavoring agent, a preservative, or the like may also be added. The medicine can also be used as a freeze-dried formulation.

The bacterium belonging to the genus *Enterococcus* can be administered by various routes, such as orally, nasally, rectally, transdermally, subcutaneously, intravenously, and intramuscularly.

The content of the bacterium belonging to the genus *Enterococcus* in the formulation varies depending on the type of the formulation, and is typically 0.001 to 100% by mass and preferably 0.01 to 100% by mass.

The dose of the bacterium belonging to the genus *Enterococcus* may be any pharmaceutically effective amount, i.e., any amount sufficient to confirm efficacy for preventing and/or treating *Pseudomonas aeruginosa* infection, and it varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, and more preferably about 6,000,000,000 to 12,000,000,000 CFU/kg body weight, in terms of the amount of the bacterium belonging to the genus *Enterococcus*, and to give one to several (e.g., 2, 3, 4, or 5 times) administrations per day. Administration period is not particularly limited and may, for example, be 7 days or more, 10 days or more, or 17 days or more.

The bacterium belonging to the genus *Enterococcus* may be added to a food. The present invention provides a food for prevention and/or treatment of *Pseudomonas aeruginosa* infection, comprising a bacterium belonging to the genus *Enterococcus*.

The following may be added to the food of the present invention: general ingredients such as protein, fat, carbohydrate, and sodium; minerals such as potassium, calcium, magnesium, and phosphorus; trace elements such as iron, zinc, copper, selenium, and chromium; vitamins such as vitamin A, β-carotene, vitamin B1, vitamin B2, vitamin B6, vitamin B12, vitamin C, niacin, folic acid, vitamin D3, vitamin E, biotin, and pantothenic acid; and other substances such as coenzyme Q10, α-lipoic acid, galacto-oligosaccharide, dietary fiber, an excipient (such as water, carboxymethyl cellulose, or lactose), a sweetener, a flavoring agent (such as malic acid, citric acid, or amino acid), and a fragrance. When the food of the present invention is provided as a liquid food, water, saline solution, fruit juice, or the like can be used as a liquid in which the food ingredients are dispersed or dissolved. In order to improve the taste in oral administration, it is recommended to use fruit juice.

The food of the present invention may be in any form such as a powder, a granule, a tablet, or a liquid. In order to allow sick or old persons to easily take the food, it is preferable for the food to be a gelled product such as jelly.

Gelling agents that can be used include thickening polysaccharides such as dextrin, agar, xanthan gum, locust bean gum, carrageenan, and pectin, gellan gum, psyllium seed gum, tara gum, guar gum, glucomannan, alginic acid, tamarind seed gum, and cellulose, and it is preferable to use one or two or more thickening polysaccharides. As regards the gel strength of the gelled product, it is preferable that the gel strength at 5° C. be 7,000±2,000 N/m². When the gel strength is 7,000±2,000 N/m², it is more preferable that the adhesion energy be 60±40 J/m³ and the cohesiveness be 0.7±0.1 J/m³. Such a gel with low adhesiveness and high cohesiveness has excellent swallowability.

The gel strength can be measured as follows. A texturometer of YAMADEN Co., Ltd. and a 16-mm-diameter plunger are used as gel strength measurement instruments, and the measurement is carried out under the following conditions: the measurement temperature is 25° C., the compression speed (the speed at which the plunger is pushed in) is 10 mm/s, the measurement strain (the ratio of the amount of pushing-in to the sample thickness) is 40.00%, the distance over which the plunger is pushed in is 10.00 mm, and the number of repetitions of pushing-in of the plunger is two.

The adhesion energy is measured as a negative energy required for pulling out the plunger after the first pushing-in of the plunger in the above gel strength measurement.

The cohesiveness is measured as the ratio between the energy at the first pushing-in and the energy at the second pushing-in in the above gel strength measurement.

The intake of the bacterium belonging to the genus *Enterococcus* may be any amount sufficient to confirm effectiveness for preventing and/or treating *Pseudomonas aeruginosa* infection, and it varies depending on the form of the formulation, the administration route, the age and body weight of the patient, the severity of the disease, and the like. In the case of an adult patient, for example, it is recommended to set the dose per administration to about 100,000,000 to 100,000,000,000 CFU/kg body weight, preferably about 1,000,000,000 to 50,000,000,000 CFU/kg body weight, and more preferably about 6,000,000,000 to 12,000,000,000 CFU/kg body weight, in terms of the amount of the bacterium belonging to the genus *Enterococcus*, and to give one to several (e.g., about 2, 3, 4, or 5 times) administrations per day.

EXAMPLES

Hereinafter, the present invention will be described in detail based on Examples. The present invention is not limited to these Examples.

Example 1

A lactic acid bacterium-containing drink was orally administered to systemic infection model mice with multi-drug resistant *Pseudomonas aeruginosa*, whereby the effect upon phylaxis of *P. aeruginosa* infection was evaluated with indicators such as survival rate.

Figure 6:
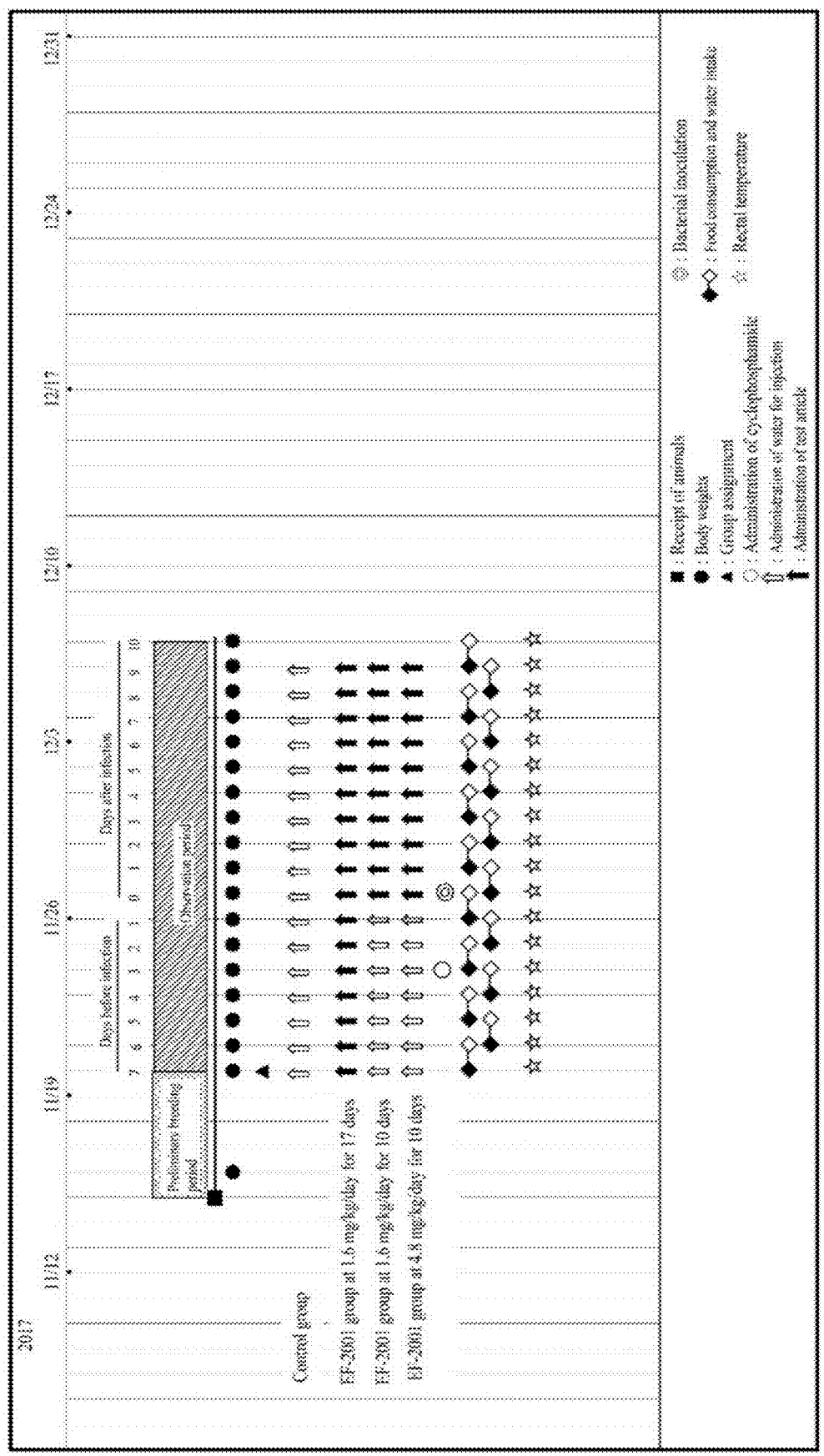
FIG. 6 shows the test schedule in Example 1.

(Test Schedule)
 The test schedule is shown in FIG. 6
(Materials and Methods)
Test Substance and Medium
 Test Substance
  Name: LACTIC ACID BACTERIA POWDER EF-2001 (Nihon Berumu Co., Ltd.) (heat-killed *E. faecalis*, 500 nm=0.5 μm in diameter)
  Properties: Yellow-brown powder
  Storage conditions: Room temperature, light-shielded, moisture-proof
  Controlled temperature: 18.0-28.0° C.
 Medium
  Name: Water for injection
  Storage Conditions: Room Temperature
  Controlled temperature: 18.0-28.0° C.
  Manufacturer: Otsuka Pharmaceutical Factory, Inc.
Sample
 Method of Preparation of Test Substance
  Lactic acid bacteria powder EF-2001 was weighed in 20 mg (electronic balance: XP205DR, Mettler-Toledo Co., Ltd.) and suspended in water for injection. The suspension was diluted to give a total volume of 125 mL with a concentration of 0.16 mg/mL. Since the lactic acid bacteria powder precipitates, it was stirred well enough to be kept suspended. Preparation was made just before use.
Pathogenic Microorganism
 Strain Used
*Pseudomonas aeruginosa* P-45 (hereinafter, referred to as "multidrug resistant *P. aeruginosa*") (released from the National Institute of Infectious Diseases)

Storage Conditions

Cryopreserved in an Ultra-cold freezer (controlled temperature: −90 to −70° C., MDF-394AT, Sanyo Electric Co., Ltd.) until use.

Reagents (1) Heart infusion broth (Eiken Chemical Co., Ltd.)
(2) NAC-agar plating medium (Eiken Chemical Co., Ltd.
(3) Physiological saline (Otsuka Pharmaceutical Plant, Inc.)

Preculture

The preserved strain of multidrug resistant *P aeruginosa* was thawed and inoculated into Heart infusion broth, then cultured in a shaking incubator (BR-23FP, Taitec Corporation, No. of shakes: 200/min) set at 37° C. under shaking for about 24 hrs. After culture, the broth was collected and centrifuged (1000 rpm, 5 min). The supernatant was discarded. The precipitate was mixed with physiological saline to give a volume of 10 mL, which served as an inoculation stock solution. This stock solution was stored in a refrigerator (controlled temperature: 2° C. to 8° C., UKS-3610DHC, Nippon Freezer Co., Ltd.) until the day of inoculation.

Viable Cell Count in the Stock Solution

The stock solution was diluted $10^2$-, $10^4$- or $10^6$-folds with physiological saline. The $10^4$- and $10^6$-fold diluted solutions were smeared on NAC-agar plating medium, and cultured in an incubator (ILE800, Yamato Scientific) set at 37° C. for a day. The number of colonies after culture was counted with a handy colony counter (CC-1, Azwan Co., Ltd.), and the number of viable bacterial cells contained in 1 ml of the stock solution was calculated.

Preparation of a Liquid Bacterial Inoculum

The stock solution was diluted with physiological saline to a concentration of $1 \times 10^7$ CFU/mL at the day of inoculation. The thus prepared bacterial solution was used as a liquid bacterial inoculum. The number of viable bacterial cells in the liquid bacterial inoculum was counted according to the method shown in the "Viable bacterial cell count in the stock solution."

Animal Test System

Animal Species, Lineage

Species: Mouse (SPF)
Lineage: BALB/c strain (BALB/c Cr Slc)
Sex, Age, and Number of Animals Acquired
Female, 4 weeks old, 44 mice
Body Weight Range 1 Day after Acquisition of Animals 12.9-18.1 g
Source
Japan SLC, Inc.

Preliminary Feeding

The animals were preliminarily fed for five days. During this period, their general condition was observed once a day and the body weight was measured twice (the day after the acquisition of animals and the final day of preliminary feeding) by electronic balance (MS3002S/02, PB3002-S/FACT, Metler Toledo Inc.). Animals with no abnormalities in body weight change and general condition were used for grouping.

Grouping Methods

The animals were stratified by body weight using a computer program (IBUKI, Nihon Bioresearch Inc.) and then at the day of grouping, random sampling was applied to ensure that the mean body weight and variance of the respective groups were approximately equal.

Identification Methods

Animals were identified by two methods in combination that were applied at the day of their acquisition: filling out on the tails with oil-based ink and painting colors on the limbs with oil-based ink. After grouping, the animals were identified by filling out animal numbers on the tails with oil-based ink. Each cage was fitted with two kinds of label, one being applied during the preliminary feeding period and filled with test number, date of animal acquisition, and animal number for preliminary feeding, and the other being color-coded labels applied after grouping and filled with test number, group name, and animal number.

Environmental Conditions and Rearing Management

Animals were reared in a room (Kiso Sansen Branch, Room No. 3) maintained at a temperature of 18-28° C. (measured value: 20-24° C.), a humidity of 30-80% (measured value: 39-67%), and light/dark periods, each 12 hours (lighting applied: 6:00 a.m. to 6:00 p.m.). Animals were reared individually in stainless steel cages (W:100×D: 160× H:80 mm) both during the preliminary feeding period and after grouping.

Cages and feeders were changed at least once a week, and water bottles and dishes were changed at least twice a week. The room was cleaned up daily by wiping and disinfecting the floor with a disinfectant-soaked mop.

Feed

The animals were fed ad libitum with a solid diet (CRF-1, Oriental Yeast Co., Ltd.) placed in feeders; the diet was manufactured within 5 months before the experiment.

Contaminant levels, bacterial counts, and nutrient contents of the diet were confirmed to meet the acceptance criteria of the test facility for each lot of diet.

Drinking Water

The animals were allowed to drink tap water ad libitum as it was supplied from a water bottle. Contaminant levels and bacterial counts of drinking water were analyzed almost every 6 months to ensure that they met the acceptance criteria of the test facility.

Administration

Route of Administration: Oral
Administration Method

A 1 mL disposable syringe (Terumo Co., Ltd.) equipped with a mouse feeding needle (FUCHIGAMI) was used to perform forced oral administration. At the time of administration, the required amount was collected by stirring the sample.

Dosage Volume, Time of Administration, Number of Doses, and Period of Administration Dosage volume: A dose of 10 mL/kg was determined by calculation based on the body weight of animal on the day of administration.

Time of administration: The administration was started at 11:00 a.m. and continued sequentially beginning from Group 1.

Number of doses: Groups 1, 2 and 3 received once-daily administration. Group 4 received once-daily administration for 7 days before inoculation and after the day of inoculation, administration was conducted three times a day for 10 days at intervals of 8 hrs.

Administration period and specifics: The day when administration started was regarded as day 1. Group 1 was administered the medium for 7 days before inoculation and 10 days from the day of inoculation. Group 2 was administered the test substance for 7 days before inoculation and 10 days from the day of inoculation. Groups 3 and 4 were administered the test substance for 10 days from the day of inoculation but administered the medium for 7 days before inoculation.

Grouping

The number of animals and group composition are shown in the table below.

| Group | Group name | Color of label | Dose (mg/kg/day) | Test Substance Administration Period | Frequency of Test Substance Dosing | Number of animals (animal number) |
|---|---|---|---|---|---|---|
| 1 | CONTROL (0 mg/125 mL) | White | 0* | 17 days including pre- and post- inoculation periods* | Once/day* | 10 (F01151-F01160) |
| 2 | LACTIC ACID BACTERIA POWDER EF-2001 (80 mg/125 mL) Whole-period administration (EF-2001 group at 1.6 mg/kg/day for 17 days) | Red | 1.6 | 17 days including pre- and post-inoculation periods | Once/day | 10 (F02251-F02260) |
| 3 | LACTIC ACID BACTERIA POWDER EF-2001 (80 mg/125 mL) Administered once after inoculation (EF-2001 group at 1.6 mg/kg/day for 10 days) | Blue | 1.6 | 10 days from the day of inoculation** | Once/day | 10 (F03351-F03360) |
| 4 | LACTIC ACID BACTERIA POWDER EF-2001 (80 mg/125 mL) Administered 3 times after inoculation (EF-2001 group at 4.8 mg/kg/day for 10 days) | Yellow | 4.8 | 10 days from the day of inoculation** | 3 times/day | 10 (F04451-F04460) |

*The medium, water for injection, was administered.
**For 7 days before inoculation, water for injection was administered once per day.
Administration to mice with lactic acid bacteria powder EF-2001 at a dose of 80 mg/125 mL once a day is equivalent to a dose of $1.2 \times 10^{10}$ CFU/kg/day.

Method of Cyclophosphamide Administration and Method of Inoculation of Bacterial Solution Four days after grouping (3 days before inoculation), cyclophosphamide (Endoxan™ for injection 100 mg; Shionogi Co., Ltd.) was administered intraperitoneally at 200 mg/kg (liquid volume: 10 mL/kg) after administration of the test substance and the medium. Seven days after grouping (3 days after cyclophosphamide administration), 0.5 mL ($5 \times 10^6$ CFU) of the liquid bacterial inoculum was inoculated intraperitoneally. The bacterial inoculum was stirred for use in each inoculation. Inoculation was performed 2 hours before administration of the test substance and the medium.

Reason for setting the bacterial inoculum cell number as indicated: Setting was done by referencing Reference[1]).

Observation and Examination

Observation of General Condition

The general condition of the mice was observed once a day before the administration of the test substance or the medium, for the period from the day of grouping to the day before the inoculation. For the period from the day of inoculation to day 3 of inoculation, the general condition was observed 4 times a day (i.e., twice in the morning before administration of the test substance or the medium and twice in the afternoon). At day 4 post-inoculation and thereafter, the general condition was observed twice a day (i.e., once in the morning before administration of the test substance or the medium and once in the afternoon); and once in the morning alone on the final day of observation. The first observation in the morning of the day of inoculation was performed before the inoculation.

Measurement of Rectal Temperature

After the day of grouping but before administration of the test substance or the medium, rectal temperature was measured with a thermometer (Physitemp, Model BAT-12, PHYSITEMP INSTRUMENTS INC.). To measure, the sensor coated with petrolatum was inserted into the anus of the mouse, and the rectal temperature was measured.

Measurement of Body Weight

Following the day of grouping, body weight was measured every day with an electronic balance (MS3002S/02, PB3002-S/FACT, Mettler-Toledo Co., Ltd.) after confirmation of the general condition.

Measurement of Feed Intake and Water Intake

Following the day of grouping, the amounts of feed and water inclusive of the feeder and water supply bottle were measured every day with an electronic balance (MS3002S/02, PB3002-S/FACT, Mettler-Toledo Co., Ltd.) and the amounts remaining in the feeder and water supply bottle were measured on the following day. Feed intake (or water intake) per day was calculated from the difference between the amount of feed (or water) and the amount remaining in the feeder (or water supply bottle).

Statistical Methods

The survival rate was calculated for each group. For the rectal temperature, body weight, feed intake and water intake, the average and standard deviation in each group were calculated.

A Fisher's exact test was used as a significance test for the survival rate on each day of observation as between the control group and each of the other groups. A Kaplan-Meier plot was drawn over the entire observation period, and generalized Wilcoxon test was conducted, with Holm corrections being made for comparisons between groups to adjust for multiplicity.

Multiple comparisons were performed as a significance test for the rectal temperature, body weight, feed intake, and water intake. That is, a test of equal variance by Bartlett method was carried out, and Tukey's test was carried out in the case of equal variance. On the other hand, when no equal variance was observed, Steel-Dwass test was used.

A hazard rate of 5% was considered significant, and separate indications were given for a hazard rate less than 5% and a hazard rate less than 1%.

A commercially available statistical program (SAS system, SAS Institute Japan) was used for the statistical analyses.

However, as regards Control Group, only one mouse survived at day 1 post-inoculation and thereafter. Since it is hard to believe that this one case represents the average value of the Group, the results at day 1 post-inoculation and thereafter that suggested the "presence" of a significant difference were excluded from evaluation and discussion.

(Test Results)
General Condition

The results of observation are shown in Table 1. For survival rate, Kaplan-Meier plots are shown in FIG. 1.

TABLE 1

| | | | | Clinical signs | | | | | | |
|---|---|---|---|---|---|---|---|---|---|---|
| | | Period for | Number of animals | Days before infection | | | | | | |
| Group | mg/kg/day | administration | and clinical signs | 7[a] | 6 | 5 | 4 | 3 | 2 | 1 |
| Control | 0 | 17 | Number of animals | 10 | 10 | 10 | 10 | 10 | 10 | 10 |
| | | | Normal | 10 | 10 | 10 | 10 | 10 | 10 | 10 |
| EF-2001 | 1.6 | 17 | Number of animals | 10 | 10 | 10 | 10 | 10 | 10 | 10 |
| | | | Normal | 10 | 10 | 10 | 10 | 10 | 10 | 10 |
| | 1.6 | 10 | Number of animals | 10 | 10 | 10 | 10 | 10 | 10 | 10 |
| | | | Normal | 10 | 10 | 10 | 10 | 10 | 10 | 10 |
| | 4.8 | 10 | Number of animals | 10 | 10 | 10 | 10 | 10 | 10 | 10 |
| | | | Normal | 10 | 10 | 10 | 10 | 10 | 10 | 10 |

[a] Start of administration in the control group and the EF-2001 group at 1.6 mg/kg/day for 17 days.

| | | | | Days after infection | | | | | | | |
|---|---|---|---|---|---|---|---|---|---|---|---|
| | | Period for | Number of ammals | 0[a] | | | | 1 | | | |
| Group | mg/kg/day | administration | and clinical signs | AM1 | AM2 | PM1 | PM2 | AM1 | AM2 | PM1 | PM2 |
| Control | 0 | 17 | Number of animals | 10 | 10 | 10 | 10 | 10 | 1 | 1 | 1 |
| | | | Normal | 10 | 10 | 1 | 1 | 0 | 0 | 0 | 0 |
| | | | Decrease in locomotor activity | 0 | 0 | 9 | 9 | 0 | 0 | 0 | 0 |
| | | | Piloerection | 0 | 0 | 9 | 9 | 1 | 1 | 1 | 1 |
| | | | Death | 0 | 0 | 0 | 0 | 9 | 0 | 0 | 0 |
| EF-2001 | 1.6 | 17 | Number of animals | 10 | 10 | 10 | 10 | 10 | 9 | 9 | 7 |
| | | | Normal | 10 | 10 | 9 | 9 | 0 | 0 | 0 | 0 |
| | | | Decrease in locomotor activity | 0 | 0 | 1 | 1 | 9 | 9 | 7 | 7 |
| | | | Piloerection | 0 | 0 | 1 | 1 | 3 | 3 | 1 | 1 |
| | | | Hypothermia | 0 | 0 | 0 | 0 | 3 | 3 | 1 | 1 |
| | | | Death | 0 | 0 | 0 | 0 | 1 | 0 | 2 | 0 |
| | 1.6 | 10 | Number of animals | 10 | 10 | 10 | 10 | 10 | 9 | 9 | 7 |
| | | | Normal | 10 | 10 | 9 | 9 | 0 | 0 | 0 | 0 |
| | | | Decrease in locomotor activity | 0 | 0 | 1 | 1 | 9 | 9 | 7 | 7 |
| | | | Piloerection | 0 | 0 | 1 | 1 | 3 | 3 | 4 | 4 |
| | | | Hypothermia | 0 | 0 | 0 | 0 | 3 | 3 | 1 | 1 |
| | | | Death | 0 | 0 | 0 | 0 | 1 | 0 | 2 | 0 |
| | 4.8 | 10 | Number of animals | 10 | 10 | 10 | 10 | 10 | 10 | 10 | 6 |
| | | | Normal | 10 | 10 | 10 | 10 | 0 | 0 | 0 | 0 |
| | | | Decrease in locomotor activity | 0 | 0 | 0 | 0 | 10 | 10 | 6 | 6 |
| | | | Piloerection | 0 | 0 | 0 | 0 | 6 | 7 | 4 | 4 |
| | | | Hypothermia | 0 | 0 | 0 | 0 | 4 | 4 | 2 | 1 |
| | | | Death | 0 | 0 | 0 | 0 | 0 | 4 | 0 | 2 |

| | | | | Days after infection | | | | | | | |
|---|---|---|---|---|---|---|---|---|---|---|---|
| | | Period for | Number of ammals | 2 | | | | 3 | | | |
| Group | mg/kg/day | administration | and clinical signs | AM1 | AM2 | PM1 | PM2 | AM1 | AM2 | PM1 | PM2 |
| Control | 0 | 17 | Number of animals | 1 | 1 | 1 | 1 | 1 | 1 | 1 | 1 |
| | | | Normal | 0 | 0 | 0 | 0 | 1 | 1 | 1 | 1 |
| | | | Decrease in locomotor activity | 0 | 0 | 0 | 0 | — | — | — | — |
| | | | Piloerection | 1 | 1 | 1 | 1 | — | — | — | — |
| | | | Death | 0 | 0 | 0 | 0 | — | — | — | — |
| EF-2001 | 1.6 | 17 | Number of animals | 7 | 5 | 5 | 5 | 5 | 5 | 5 | 5 |
| | | | Normal | 0 | 0 | 0 | 0 | 5 | 5 | 5 | 5 |
| | | | Decrease in locomotor activity | 5 | 5 | 5 | 5 | — | — | — | — |
| | | | Piloerection | 1 | 1 | 1 | 1 | — | — | — | — |
| | | | Hypothermia | 0 | 0 | 0 | 0 | — | — | — | — |
| | | | Death | 2 | 0 | 0 | 0 | — | — | — | — |
| | 1.6 | 10 | Number of animals | 7 | 3 | 3 | 3 | 3 | 3 | 3 | 3 |
| | | | Normal | 0 | 0 | 0 | 0 | 2 | 2 | 2 | 3 |
| | | | Decrease in locomotor activity | 3 | 3 | 3 | 3 | 1 | 1 | 1 | — |
| | | | Piloerection | 1 | 1 | 1 | 1 | — | — | — | — |
| | | | Hypothermia | 0 | 0 | 0 | 0 | — | — | — | — |
| | | | Death | 4 | 0 | 0 | 0 | — | — | — | — |
| | 4.8 | 10 | Number of animals | 6 | 4 | 4 | 4 | 4 | 4 | 4 | 4 |
| | | | Normal | 0 | 0 | 0 | 0 | 4 | 4 | 4 | 4 |

TABLE 1-continued

| Clinical signs | | | | | | | | |
|---|---|---|---|---|---|---|---|---|
| Decrease in locomotor activity | 4 | 4 | 4 | 4 | — | — | — | — |
| Piloerection | 3 | 2 | 2 | 2 | — | — | — | — |
| Hypothermia | 0 | 0 | 0 | 0 | — | — | — | — |
| Death | 2 | 0 | 0 | 0 | — | — | — | — |

AM1: 1st observation in the morning.
AM2: 2nd observation in the morning.
PM1: 1st observation in the afternoon.
PM2: 2nd observation in the afternoon.
AM: Morning
PM: Afternoon
[a)]Start of administration in the EF-2001 group at 1.6 mg/kg/day for 10 days and 4.8 mg/kg/day for 10 days.

| | | | | Days after infection | | | | | |
|---|---|---|---|---|---|---|---|---|---|
| | | Period for | Number of animals | 4 | | 5 | | 6 | |
| Group | mg/kg/day | administration | and clinical signs | AM | PM | AM | PM | AM | PM |
| Control | 0 | 17 | Number of animals | 1 | 1 | 1 | 1 | 1 | 1 |
| | | | Normal | 1 | 1 | 1 | 1 | 1 | 1 |
| | | | Decrease in locomotor activity | — | — | — | — | — | — |
| | | | Piloerection | — | — | — | — | — | — |
| | | | Death | — | — | — | — | — | — |
| EF-2001 | 1.6 | 17 | Number of animals | 5 | 5 | 5 | 5 | 5 | 5 |
| | | | Normal | 5 | 5 | 5 | 5 | 5 | 5 |
| | | | Decrease in locomotor activity | — | — | — | — | — | — |
| | | | Piloerection | — | — | — | — | — | — |
| | | | Hypothermia | — | — | — | — | — | — |
| | | | Death | — | — | — | — | — | — |
| | 1.6 | 10 | Number of animals | 3 | 3 | 3 | 3 | 3 | 3 |
| | | | Normal | 3 | 3 | 3 | 3 | 3 | 3 |
| | | | Decrease in locomotor activity | — | — | — | — | — | — |
| | | | Piloerection | — | — | — | — | — | — |
| | | | Hypothermia | — | — | — | — | — | — |
| | | | Death | — | — | — | — | — | — |
| | 4.8 | 10 | Number of animals | 4 | 4 | 4 | 4 | 4 | 4 |
| | | | Normal | 4 | 4 | 4 | 4 | 4 | 4 |
| | | | Decrease in locomotor activity | — | — | — | — | — | — |
| | | | Piloerection | — | — | — | — | — | — |
| | | | Hypothermia | — | — | — | — | — | — |
| | | | Death | — | — | — | — | — | — |

| | | | | Days after infection | | | | | | |
|---|---|---|---|---|---|---|---|---|---|---|
| | | Period for | Number of animals | 7 | | 8 | | 9 | | 10 |
| Group | mg/kg/day | administration | and clinical signs | AM | PM | AM | PM | AM | PM | AM |
| Control | 0 | 17 | Number of animals | 1 | 1 | 1 | 1 | 1 | 1 | 1 |
| | | | Normal | 1 | 1 | 1 | 1 | 1 | 1 | 1 |
| | | | Decrease in locomotor activity | — | — | — | — | — | — | — |
| | | | Piloerection | — | — | — | — | — | — | — |
| | | | Death | — | — | — | — | — | — | — |
| EF-2001 | 1.6 | 17 | Number of animals | 5 | 5 | 5 | 5 | 5 | 5 | 5 |
| | | | Normal | 5 | 5 | 5 | 5 | 5 | 5 | 5 |
| | | | Decrease in locomotor activity | — | — | — | — | — | — | — |
| | | | Piloerection | — | — | — | — | — | — | — |
| | | | Hypothermia | — | — | — | — | — | — | — |
| | | | Death | — | — | — | — | — | — | — |
| | 1.6 | 10 | Number of animals | 3 | 3 | 3 | 3 | 3 | 3 | 3 |
| | | | Normal | 3 | 3 | 3 | 3 | 3 | 3 | 3 |
| | | | Decrease in locomotor activity | — | — | — | — | — | — | — |
| | | | Piloerection | — | — | — | — | — | — | — |
| | | | Hypothermia | — | — | — | — | — | — | — |
| | | | Death | — | — | — | — | — | — | — |
| | 4.8 | 10 | Number of animals | 4 | 4 | 4 | 4 | 4 | 4 | 4 |
| | | | Normal | 4 | 4 | 4 | 4 | 4 | 4 | 4 |
| | | | Decrease in locomotor activity | — | — | — | — | — | — | — |
| | | | Piloerection | — | — | — | — | — | — | — |
| | | | Hypothermia | — | — | — | — | — | — | — |
| | | | Death | — | — | — | — | — | — | — |

AM: Morning, PM: Afternoon.

The observation of the general condition showed piloerection and decrease in locomotion in all groups. Hypothermia was observed in the whole-period administration group, the post-inoculation administration group, and the post-inoculation three times administration group. Further, death was observed in all groups from day 1 to 2 post-inoculation.

In the control group, 9 out of 10 cases showed decrease in locomotion and piloerection on the day of inoculation; and 9 out of 10 cases died at day 1 post-inoculation. Although piloerection was observed in one out of one case from day 1 to 2 post-inoculation, no abnormality was observed at day 3 post-inoculation and thereafter. Survival rate was 10%.

In the whole-period administration group, piloerection and decrease in locomotion were observed in one out of 10 cases on the day of inoculation. On the first observation in the morning at day 1 post-inoculation, piloerection and hypothermia were observed in 3 out of 10 cases and decrease in locomotion in 9 out of 10 cases. By the second observation in the afternoon of the same day, 3 out of 10 cases died. At day 2 post-inoculation, 2 out of 7 cases died, and piloerection or decrease in locomotion was observed in the surviving mice, whereas no abnormalities were observed at day 3 post-inoculation and thereafter. Survival rate was 50%. Compared to the control group, a significantly high value (Fisher's exact test) was observed at day 1 post-inoculation, and a significantly high value (generalized Wilcoxon) was observed throughout the observation period.

In the post-inoculation once administration group, piloerection and decrease in locomotion were observed in 1 out of 10 cases on the day of inoculation. On the first observation in the morning at day 1 post-inoculation, piloerection and hypothermia were observed in 3 out of 10 cases, and decrease in locomotion was observed in 9 out of 10 cases. By the second observation of the afternoon, 3 out of 10 cases died. At day 2 post-inoculation, 4 out of 7 cases died, and piloerection or decrease in locomotion was observed in the surviving mice. Although decrease in locomotion was observed at day 3 post-inoculation, no abnormalities were recognized at day 4 post-inoculation and thereafter. Survival rate was 30%. Compared to the control group, a significantly high value (Fisher's exact test) was observed at day 1 post-inoculation, and a significantly high value (generalized Wilcoxon) was observed throughout the observation period.

In the post-inoculation three times administration group, no abnormalities were observed on the day of inoculation; however, on the first observation in the morning at day 1 post-inoculation, piloerection was observed in 6 out of 10 cases, decrease in locomotion in 10 out of 10 cases, and hypothermia in 4 out of 10 cases. By the second observation in the afternoon, 4 out of 10 cases died. At day 2 post-inoculation, 2 out of 6 cases died, and decrease in locomotion or piloerection was observed in the surviving mice, but no abnormalities were recognized at day 3 post-inoculation and thereafter. Survival rate was 40%. Compared to the control group, a significantly high value (generalized Wilcoxon) was observed throughout the observation period.

Measurement of Rectal Temperature

Figure 2:
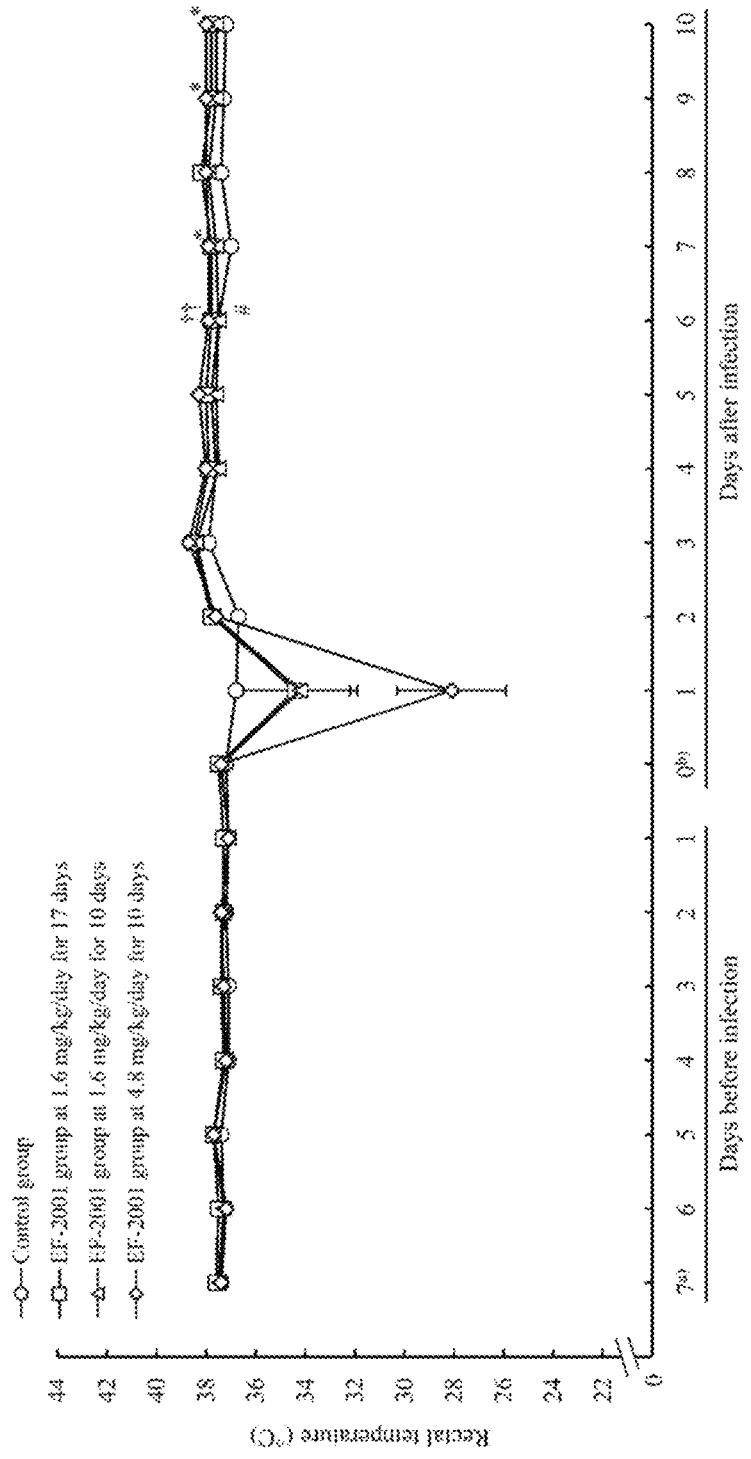
FIG. 2 shows test results (rectal temperature) in Example 1.

The results are shown in FIG. 2.

In the control group, the mean rectal temperature continued to decrease from the day of inoculation until day 2 post-inoculation, showing a 0.5° C. decrease in two days (the number of survival cases (n) was 1 in the control group at day 1 post-inoculation and thereafter).

In the whole-period administration group, the mean rectal temperature decreased by 3.1° C. from the day of inoculation until day 1 post-inoculation. However, in the 5 cases which escaped death, the temperature at day 1 post-inoculation increased (day of inoculation: 37.6° C.; day 1 post-inoculation: 38.3° C.) and the subsequent trend was approximate to the temperature on the day of inoculation.

In the post-inoculation once administration group, the mean rectal temperature showed a 3.2° C. decrease from the day of inoculation until day 1 post-inoculation. However, in the 3 cases which escaped death, the temperature at day 1 post-inoculation increased (day of inoculation: 37.4° C.; day 1 post-inoculation: 38.8° C.) and the subsequent trend was approximate to the temperature on the day of inoculation. When compared to the whole-period administration group at day 6 post-inoculation, a significantly low value was recognized.

In the post-inoculation three times administration group, the mean rectal temperature showed a 9.3° C. decrease from the day of inoculation until day 1 post-inoculation. However, in 3 out of the 4 cases (excluding F04457) which escaped death, the temperature at day 1 post-inoculation increased (day of inoculation: 37.0° C.; day 1 post-inoculation: 37.9° C.) and the subsequent trend was approximate to the temperature on the day of inoculation. Compared to the control group, a significantly high value was recognized at day 7, 9 and 10 post-inoculation. Further, compared to the post-inoculation once administration group at day 6 post-inoculation, a significantly high value was recognized.

Body Weight

Figure 3:
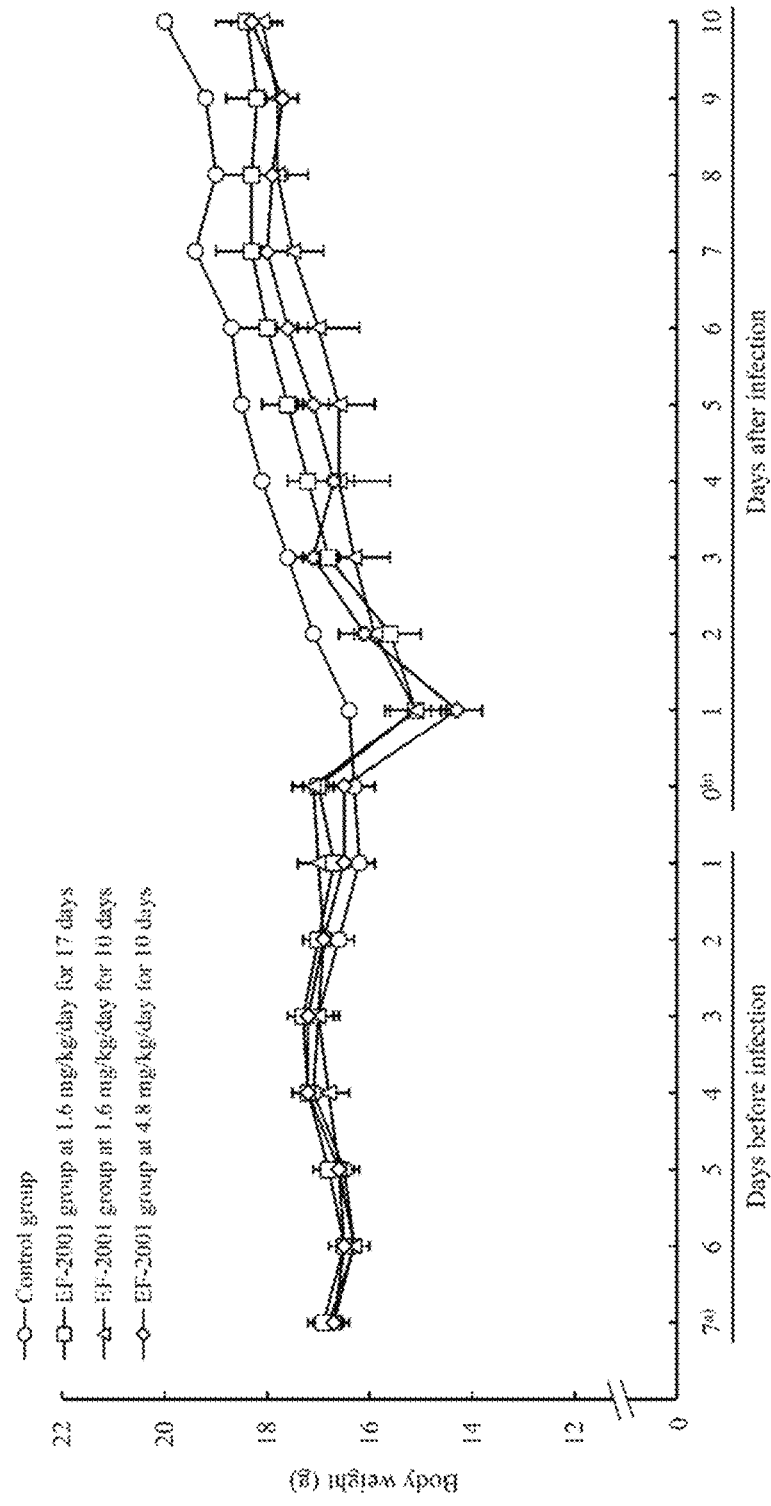
FIG. 3 shows test results (body weight) in Example 1.

The results are shown in FIG. 3.

In the control group, the mean body weight changed steadily (the number of survival cases (n) was 1 in the control group at day 1 post-inoculation and thereafter).

In the whole-period administration group, the mean body weight decreased by 1.9 g at day 1 post-inoculation, but in the 5 cases which escaped death, the decrease was smaller (day of inoculation: 17.5° C.; day 1 post-inoculation: 16.3° C.). Thereafter, their body weight changed steadily.

In the post-inoculation once administration group, the mean body weight decreased by 2.0 g at day 1 post-inoculation, but in the 3 cases which escaped death, the decrease was smaller (day of inoculation: 17.3° C.; day 1 post-inoculation: 15.9° C.). Thereafter, their body weight changed steadily.

In the post-inoculation three times administration group, the mean body weight decreased by 2.2 g at day 1 post-inoculation, but in the 4 cases which escaped death, the decrease was smaller (day of inoculation: 17.1° C.; day 1 post-inoculation: 15.6° C.). Thereafter, their body weight changed steadily.

Feed Intake

Figure 4:
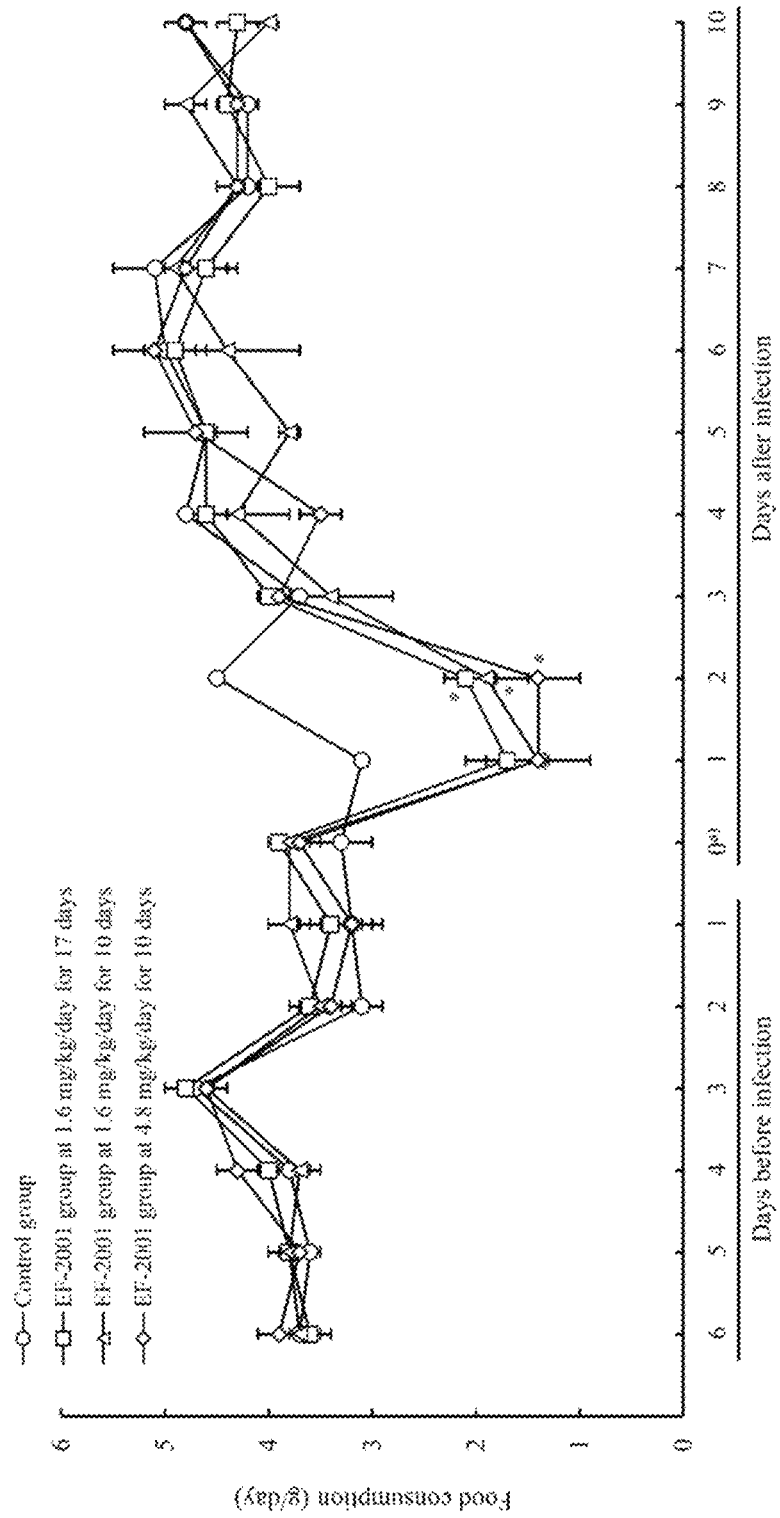
FIG. 4 shows test results (feed intake) in Example 1.

The results are shown in FIG. 4.

In the control group, changes in the mean feed intake were small (the number of survival cases (n) was 1 in the control group at day 1 post-inoculation and thereafter).

In the whole-period administration group, the mean feed intake decreased by 2.2 g at day 1 post-inoculation, but recovered thereafter. Compared to the control group, a significantly low value was recognized at day 2 post-inoculation.

In the post-inoculation once administration group, the mean feed intake decreased by 2.4 g at day 1 post-inoculation, but recovered thereafter. Compared to the control group, a significantly low value was recognized at day 2 post-inoculation.

In the post-inoculation three times administration group, the mean feed intake decreased by 2.3 g at day 1 post-inoculation, but recovered thereafter. Compared to the control group, a significantly low value was recognized at day 2 post-inoculation.

Water Intake

Figure 5:
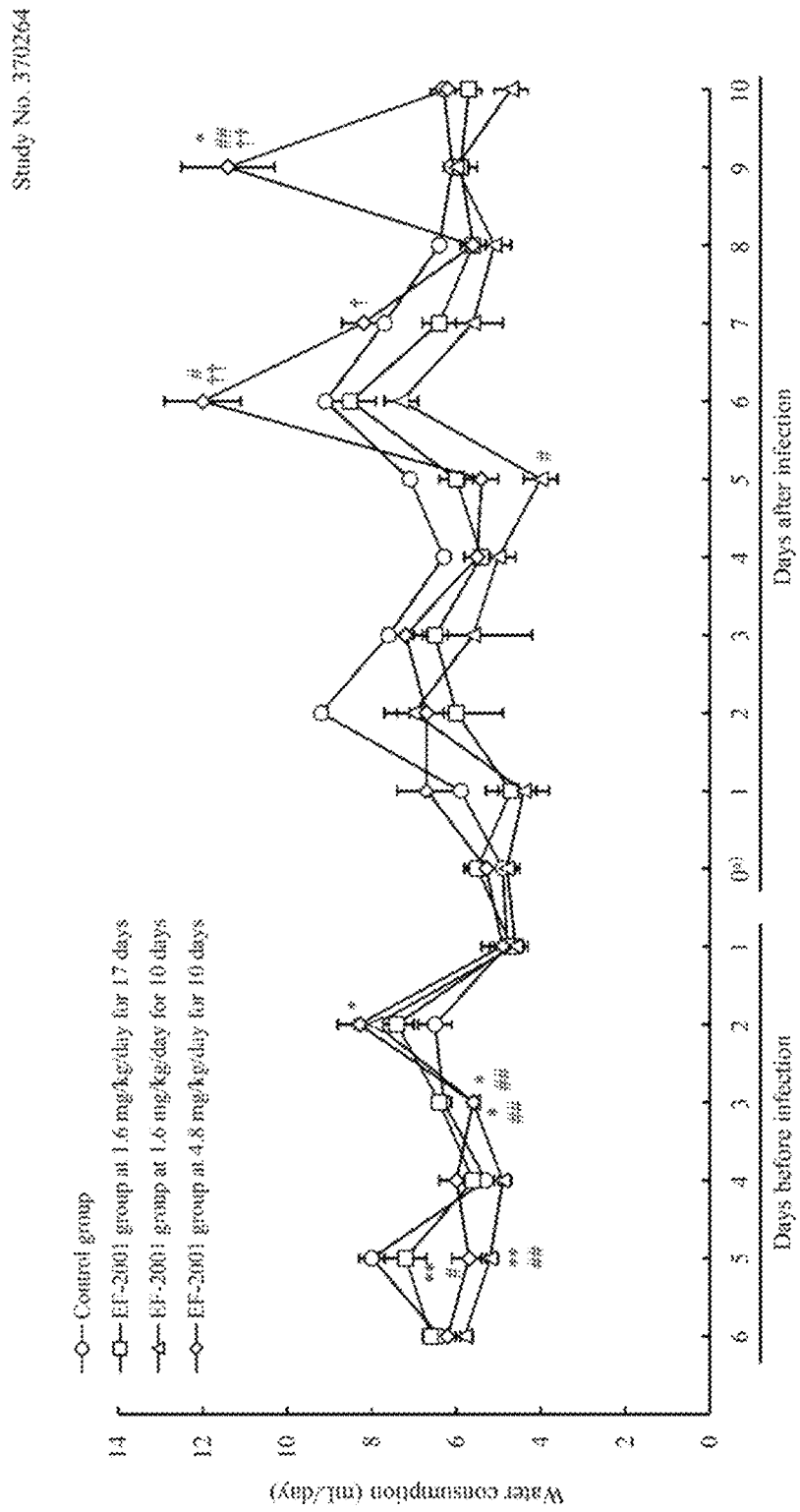
FIG. 5 shows test results (water intake) in Example 1.

The results are shown in FIG. 5.

In the control group, changes in the mean water intake were small (the number of survival cases (n) was 1 in the control group at day 1 post-inoculation and thereafter).

In the whole-period administration group, the mean water intake decreased by 0.8 ml at day 1 post-inoculation but recovered thereafter.

In the post-inoculation once administration group, the mean water intake decreased by 0.4 ml at day 1 post-inoculation but recovered thereafter. Compared to the control group, significantly low values were recognized at day 5 and 3 pre-inoculation. Further, compared to the whole-period administration group, a significantly low value was recognized at day 5 post-inoculation and significantly low values were also recognized at day 5 and 3 pre-inoculation.

In the post-inoculation three times administration group, no decrease was observed in the mean water intake at day 1 post-inoculation. Compared to the control group, significantly low values were recognized at day 5 and 3 pre-inoculation and significantly high values were recognized at day 2 pre-inoculation and day 9 post-inoculation. Further, compared to the whole-period administration group, significantly high values were recognized at day 6 and 9 post-inoculation and significantly low values were recognized at day 5 and 3 pre-inoculation. Compared to post-inoculation once administration group, significantly high values were recognized at day 6, 7 and 9 post-inoculation.

(Discussion)

A lactic acid bacterium-containing drink was orally administered to systemic infection model mice with multidrug resistant *Pseudomonas aeruginosa* and the effects the timings of *P. aeruginosa* infection and the start of administration as well as the dose of administration would have upon phylaxis were evaluated by survival rate and other indicators in order to examine the most efficient intake conditions.

While abnormalities in the general condition were observed in 9 out of 10 cases in the control group on the day of *P. aeruginosa* inoculation, all of the three groups which were administered a powder of a lactic acid bacterium developed abnormalities in the general condition only in a small number of cases (0 out of 10 cases or 1 out of 10 cases) on the day of *P. aeruginosa* inoculation. On the other hand, the developed symptoms disappeared in the control group at day 3 post-inoculation which was no different than in the lactic acid bacterium powder administration groups. The timing of disappearance was also no different among the lactic acid bacterium powder administration groups.

The survival rate was 10% in the control group (9 out of 10 cases died), whereas it was 50% in the whole-period administration group (5 out of 10 cases died), 30% in the post-inoculation once administration group (7 out of 10 cases died), and 40% in the post-inoculation three times administration group (6 out of 10 cases died), with the result that all of the lactic acid bacterium powder administration groups showed a significant rise in survival rate.

As for body weight, rectal temperature, feed intake and water intake, only one mouse survived in the control group at day 1 post-inoculation, reducing the accuracy of comparison with the control group in the period of interest (i.e., at day 1 post-inoculation and thereafter), so the present inventors did not consider those effects to have been caused by the administration of the lactic acid bacterium powder. As regards decrease in body weight and rectal temperature, the effect was strong in dead mice and weak in surviving mice. As for the changes in body weight, rectal temperature, feed intake and water intake, no difference was found among the lactic acid bacterium powder administration groups.

As described above, it was survival rate that was found to differ among the lactic acid bacterium powder administration groups in terms of the effect upon phylaxis. The survival rate was the highest in the whole-period administration group, followed by the post-inoculation three times administration group and the post-inoculation once administration group in this order. Therefore, the most efficient intake condition was continuous administration from pre-infection to post-infection stages. Subsequently, although the difference is only based on one case of death, the present inventors considered 4.8 mg/kg/day (post-inoculation three times administration) to be more effective than a single administration of 1.6 mg/kg/day (post-inoculation once administration).

From the foregoing, it has been demonstrated that intake of lactic acid bacterium powder EF-2001 (a component of the lactic acid bacterium-containing drink) is the most effective for phylaxis if its ingestion is started before infection with multidrug *P. aeruginosa* and continued after such infection. Even when the bacterium powder was ingested after infection, dose-dependent efficacy was observed but the effect was limited as compared to the case of starting ingestion before infection.

REFERENCE

1) T. Hirai et al., Therapeutic Effect of Non-remunerated Voluntary Blood Donation-derived Intravenous Human Immunoglobulin G (IVIG) on the Treatment of Experimental Bacterial Infections-II. Preventive Effect of IVIG on Experimental *Pseudomonas aeruginosa* Infection in Neutropenic Mice, Clinical Pharmacology and Therapy, Vol. 16 (2), 141-149, 2006

All publications, patents and patent applications cited herein are incorporated herein by reference in their entirety.

INDUSTRIAL APPLICABILITY

The present invention is applicable to prevention and/or treatment of *Pseudomonas aeruginosa* infection.

The invention claimed is:

1. A method for treatment of *Pseudomonas aeruginosa* infection, comprising administering to a subject a pharmaceutically effective amount of a bacterium *Enterococcus faecalis* EF-2001 strain that is killed.

2. The method according to claim 1, wherein the bacterium is orally administered.

3. The method according to claim 2, wherein the bacterium is orally administered in an amount of $1 \times 10^8$-$1 \times 10^{11}$ CFU/kg body weight per dose.

4. The method according to claim 3, wherein the bacterium is orally administered one or more times per day in an amount of $1 \times 10^8$-$1 \times 10^{11}$ CFU/kg body weight per dose.

5. The method according to claim 4, wherein the is orally administered one to five times per day in an amount of $1 \times 10^9$-$1 \times 10^{11}$ CFU/kg body weight per dose.

6. The method according to claim 2, wherein the bacterium is orally administered in an amount of $1 \times 10^9$-$5 \times 10^{10}$ CFU/kg body weight per dose.

7. The method according to claim 6, wherein the bacterium is orally administered one or more times per day in an amount of $1 \times 10^9$-$5 \times 10^{10}$ CFU/kg body weight per dose.

8. The method according to claim 7, wherein the bacterium is orally administered one to five times per day in an amount of $1 \times 10^9$-$5 \times 10^{10}$ CFU/kg body weight per dose.

9. The method according to claim 2, wherein the bacterium is orally administered in an amount of $1.2 \times 10^{10}$ or more CFU/kg body weight per dose.

10. The method according to claim 9, wherein the bacterium is orally administered one or more times per day in an amount of $1.2 \times 10^{10}$ or more CFU/kg body weight per dose.

11. The method according to claim 10, wherein the bacterium is orally administered one to five times per day in an amount of $1.2 \times 10^{10}$ or more CFU/kg body weight per dose.

12. The method according to claim 2, wherein the bacterium is orally administered for seven or more days.

13. A method of treating *Pseudomonas aeruginosa* infection in a subject in need thereof, comprising administering to the subject a pharmaceutically effective amount of a bacterium *Enterococcus faecalis* EF-2001 strain.

14. The method according to claim 1, wherein the killed *Enterococcus faecalis* is prepared in a format selected from the group consisting of a tablet, a capsule, a powder, a granule, a liquid, a syrup, an aerosol, a suppository, or an injection.

15. The method according to claim 14, wherein the killed *Enterococcus faecalis* is mixed with one or more selected from the group consisting of water, vegetable oil, a sugar, a starch, a cellulose derivative, a lubricant, a binder, a disintegrant, an antioxidant, a colorant, a flavoring agent, and a preservative.

16. The method according to claim 1, wherein the killed *Enterococcus faecalis* is added to a food that is administered to the subject.

17. The method according to claim 16, wherein the food is a gelled product comprising one or more selected from the group consisting of dextrin, agar, xanthan gum, locust bean gum, carrageenan, pectin, gellan gum, *psyllium* seed gum, tara gum, guar gum, glucomannan, alginic acid, tamarind seed gum, and cellulose.

18. The method according to claim 17, wherein the gelled product has a gel strength of $7,000 \pm 2,000$ N/m$^2$ at 5° C.

19. The method of claim 18, wherein the gelled product has an adhesion energy of $60 \pm 40$ J/m$^3$ and the cohesiveness be $0.7 \pm 0.1$ J/m$^3$.

20. The method of claim 1, wherein the killed *Enterococcus faecalis* is administered without propolis or royal jelly.

* * * * *